United States Patent
Fitton

(10) Patent No.: US 6,536,424 B2
(45) Date of Patent: Mar. 25, 2003

(54) ANATOMICAL MOUTHPIECE WITH RETAINING WINGS AND METHOD OF USE

(76) Inventor: Russell P. Fitton, 820 S. Northwest Hwy., Barrington, IL (US) 60010

( * ) Notice: Subject to any disclaimer, the term of this patent is extended or adjusted under 35 U.S.C. 154(b) by 0 days.

(21) Appl. No.: 09/881,338

(22) Filed: Jun. 14, 2001

(65) Prior Publication Data
US 2002/0189613 A1 Dec. 19, 2002

(51) Int. Cl.$^7$ .................. A61M 15/00; A61M 16/00; A62B 18/08; A61F 11/00; A61C 5/14
(52) U.S. Cl. .................. 128/200.24; 128/857; 128/848; 128/859; 128/860; 128/861; 128/862; 128/204.23; 128/206.29
(58) Field of Search ................ 128/857, 848, 128/859–862, 200.24, 204.23, 206.29; 602/902

(56) References Cited

U.S. PATENT DOCUMENTS

| | | | |
|---|---|---|---|
| 3,603,306 A | | 9/1971 | Bonin, Jr. |
| 3,844,281 A | | 10/1974 | Shamlian |
| 4,862,903 A | | 9/1989 | Campbell |
| 5,062,422 A | | 11/1991 | Kinkade |
| 5,117,817 A | * | 6/1992 | Lin .................. 128/201.11 |
| 5,203,324 A | | 4/1993 | Kinkade |
| 5,305,741 A | | 4/1994 | Moles |
| 5,438,978 A | * | 8/1995 | Hardester, III ......... 128/201.13 |
| 5,701,885 A | * | 12/1997 | Hale .................. 128/201.26 |
| 5,865,170 A | * | 2/1999 | Moles .................. 128/201.26 |
| 6,371,108 B1 | * | 4/2002 | Christianson ......... 128/201.11 |

OTHER PUBLICATIONS

Barclay, Laurie, "Scuba Mouthpiece Can Cause Jaw and Dental Problems" WebMDHealth, available at http://my.webmd.com/content/article/1676.52711, pp. 1–3; visited May 14, 2001.

* cited by examiner

Primary Examiner—Steven O. Douglas
Assistant Examiner—Anuradha Ramana
(74) Attorney, Agent, or Firm—Brinks Hofer Gilson & Lione

(57) ABSTRACT

A mouthpiece includes a wall having an anterior section and a plurality of posterior sections. Retaining wings are coupled to the anterior section. The retaining wings conform to the anatomy of the user's labial and buccal vestibule that extends between the user's upper and lower jaws and the interior surfaces of the user's cheeks. The method of using the mouthpiece includes grasping the continuous wall, flexing the retaining wings toward ends of the posterior sections, and inserting the retaining wings into the user's mouth.

28 Claims, 4 Drawing Sheets

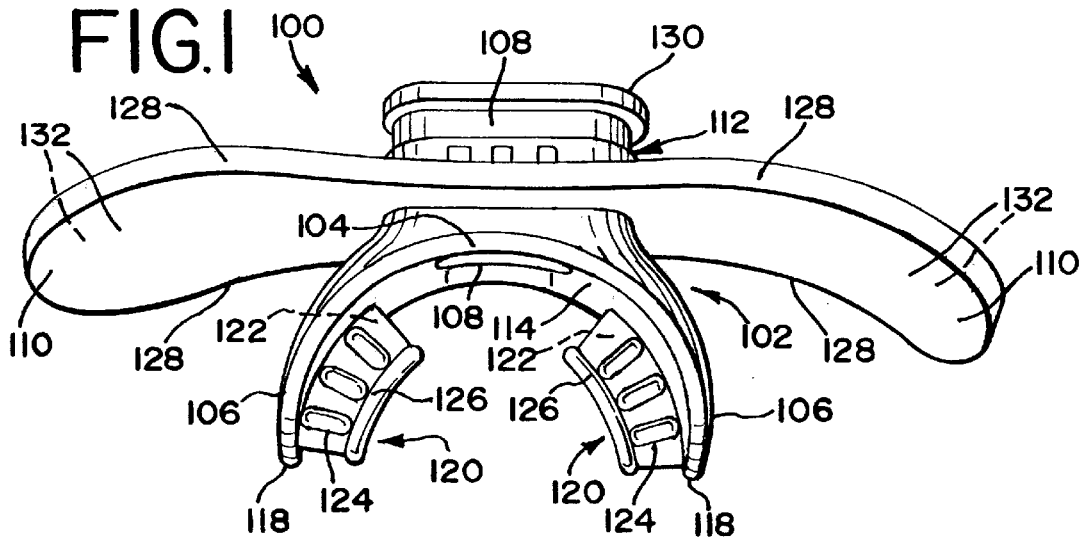
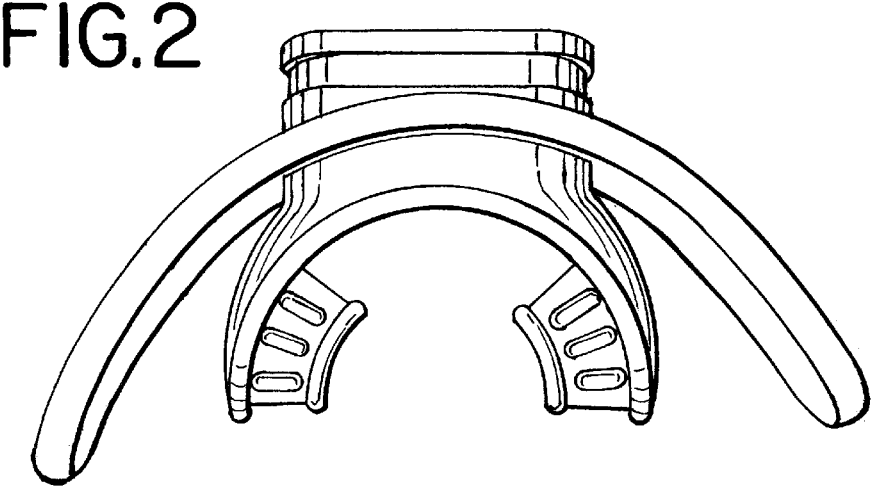
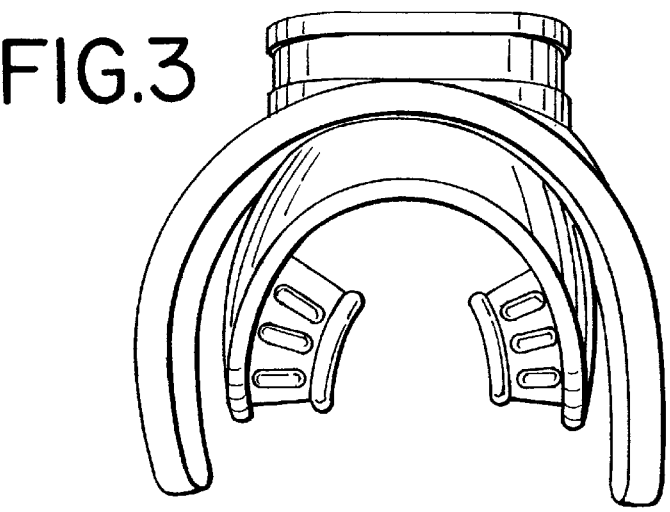

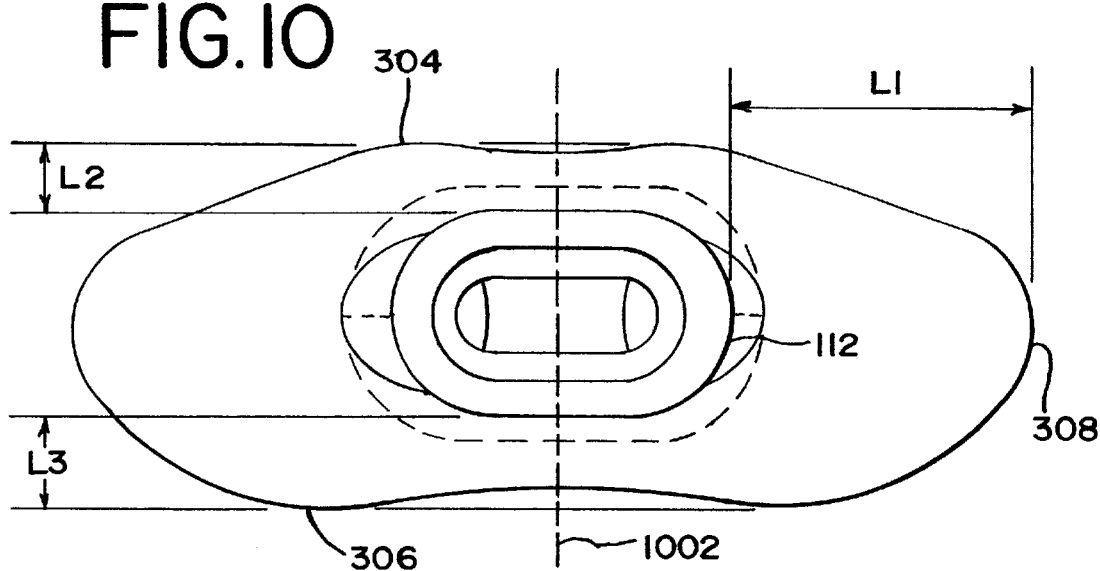
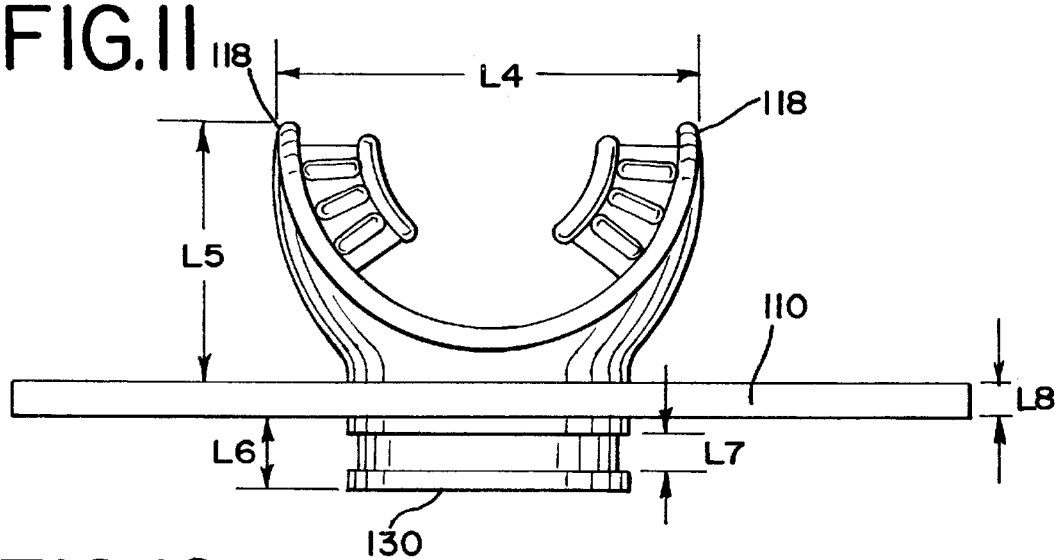
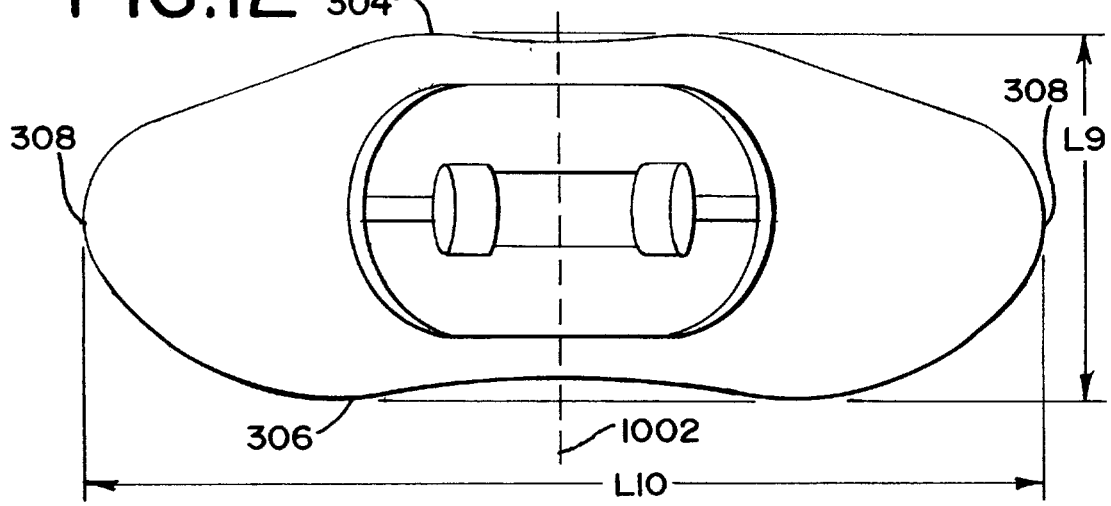

US 6,536,424 B2

ANATOMICAL MOUTHPIECE WITH RETAINING WINGS AND METHOD OF USE

BACKGROUND

This invention relates to a mouthpiece, and more particularly, to a mouthpiece and method of use for breathing or medical treatments.

Mouthpieces allow users to breath from an apparatus that delivers gas. In some medical devices, mouthpieces allow for the infusion of gas to oxygenate the lungs and expiratory pressures that draw carbon dioxide and other gases from the lungs. In underwater uses, mouthpieces allow swimmers to breath from an apparatus that delivers gas at the same pressure as the surrounding water.

Some underwater mouthpieces have not changed over a long period of time. Bite blocks gripped by front and middle teeth can be used to secure some mouthpieces to the interior cavity of the mouth. This gripping pressure by the front and middle teeth can cause joint stress and inflammation. A prolonged use can result in temporomandibular joint syndrome that generates symptoms such as severe headaches, muscle fatigue, facial pain, and ringing in the ears. When underwater mouthpieces affect swimmers' ears, balance can be affected and underwater accidents such as drowning can occur. In addition, underwater mouthpieces can result in gum abrasions, bone loss, and damage to restorative dental work.

Some underwater mouthpieces can also add significant resistance to swimmers' respiratory systems. Because these underwater mouthpieces are retained by clenched jaws the normal movement of airflow through the mouth is reduced. This decreased ventilation is complicated by the diminished breathing capacity that occurs with changes in water depth. Accordingly, carbon dioxide levels in swimmers can increase which impair swimmers' consciousness and can lead to drowning. The present invention is directed to a mouthpiece and a method of use that overcomes some of these potential drawbacks in the prior art.

BRIEF DESCRIPTION OF THE DRAWINGS

In the figures, like reference numerals designate similar parts throughout several views.

FIG. 1 is a side perspective view of a presently preferred embodiment.

FIG. 2 is a top view of FIG. 1.

FIG. 3 is a second a top view of FIG. 1.

FIG. 10 is a second front view of FIG. 1.

FIG. 11 is a third top view of FIG. 1.

FIG. 12 is a second rear view of FIG. 1.

SUMMARY

Figure 4:
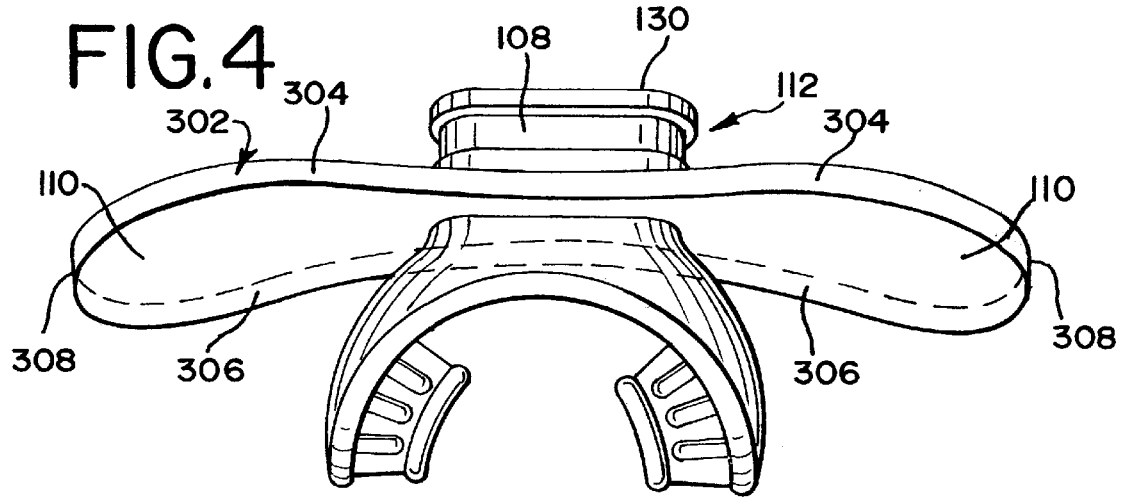
FIG. 4 is a second side perspective view of the presently preferred embodiment.

A presently preferred mouthpiece includes a wall having an anterior and a plurality of posterior sections. The anterior and posterior sections have an inner surface that conforms to the anatomy of a user's upper and lower dental arches. The anterior section further encloses an orifice. Retaining wings are coupled to the anterior section. The retaining wings include a portion that conforms to the anatomy of a user's labial and buccal vestibule that extends between the user's upper and lower jaws and interior surfaces of the user's cheeks.

A presently preferred method of using the mouthpiece includes grasping the wall, flexing the retaining wings toward ends of the posterior sections, and inserting the retaining wings into the user's mouth.

DETAILED DESCRIPTION OF THE PRESENTLY PREFERRED EMBODIMENTS

The presently preferred mouthpiece is a device that facilitates breathing. In medical treatments, the presently preferred mouthpiece allows devices and peripheral systems to deliver oxygen and other treatments to the lungs and remove carbon dioxide or other by-products from the lungs. The presently preferred mouthpiece facilitates fluid flow to the lungs. In underwater uses, the presently preferred mouthpiece allows swimmers to breath underwater for extended periods of time. The mouthpiece reduces the breathing resistance of some prior art mouthpieces.

FIG. 1 is a perspective view of a presently preferred embodiment. The presently preferred mouthpiece 100 comprises a continuous peripheral flexible wall 102 having an anterior section 104 and a plurality of posterior sections 106. Preferably, the inner and outer surfaces of the anterior and posterior sections 104 and 106 are customized to the anatomy of a user's upper and lower dental arches. Preferably, the posterior sections 106 have substantially smaller heights than the anterior section 104. As shown, the height of the anterior section 104 tapers down to the shorter heights of the posterior sections 106. Preferably, the anterior section 104 encloses an orifice 108 that passes through the anterior section 104 and retaining wings 110. Preferably, the orifice 108 is partially enclosed by a neck 112 that projects from an outer surface of the anterior section 104.

Preferably, the inner surfaces of the anterior and posterior sections 104 and 106 have a U-shape. A curved channel 114 extends along the inner surfaces from the orifice 108 to the ends 118 of the posterior sections 106. Preferably, the curved channel 114 aligns with a user's exterior dental curve from a central incisor to a third molar. As shown, a plurality of bitewings 120 divide a portion of the curved channel 114 into upper and lower channels at intermediate positions between the anterior section 104 and the ends 118 of the posterior sections 106. Each bitewing 120 includes a pair of upper and lower surfaces 122 and 124 that extend inward to an adjoining wall 126. While the upper and lower surfaces 122 and 124 of the bitewings 120 are shown substantially flat in FIG. 1, alternative presently preferred embodiments can include contoured upper and/or lower surfaces 122 and 124. For example, referring to FIGS. 2, 3, 7, and 11, the contour can comprise spaced apart upper and lower recesses. Preferably, the recesses have a substantially curved or elliptical shape angled to the user's upper and lower dental arch. More preferably, the recesses are fitted to a user's upper and lower molars and bicuspids. In another presently preferred alternative embodiment, the recesses can be positioned exclusively on the upper or lower surfaces 122 and 124, or on any combination of the upper and lower surfaces 122 and 124 of the bitewings 120.

Referring to FIG. 1, preferably the upper and lower surfaces 122 and 124 of the bitewings 120 include a curved transition to a portion of the inner surfaces of the posterior sections 106 and the adjoining wall 126. Preferably, the height of the adjoining wall 126 varies with the user's anatomy. Preferably, the adjoining wall 126 is spaced apart from the inner surface of the posterior section 106 and can be aligned with the inner dental curve or inner dental arch of the user. In the presently preferred embodiment, preferably the adjoining wall 126 can be positioned adjacent to or in contact with the inner surfaces of the user's molars or bicuspids.

Figure 9:
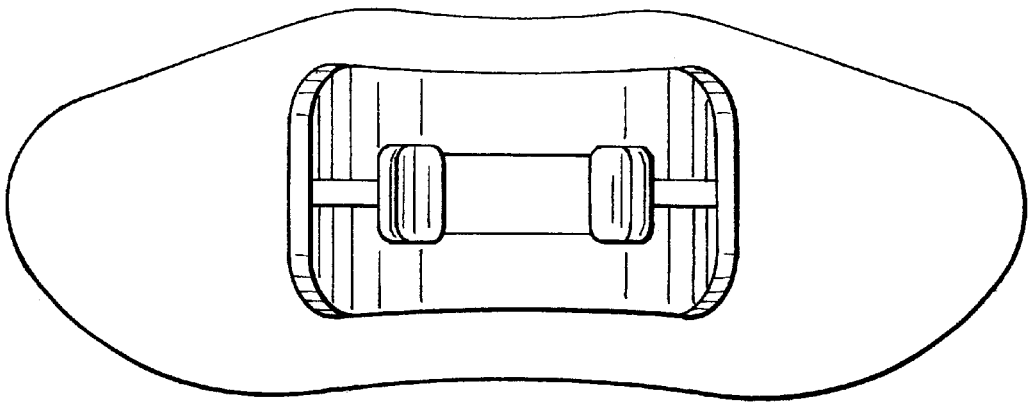
FIG. 9 is a rear view of FIG. 1.

Preferably, the retaining wings 110 have a substantially obround shape framed by a continuous surface 128 that can be positioned within a labial and buccal vestibule of the user. The labial and buccal vestibule is bounded in front and laterally by the user's lips and the continuous mucous membrane that lines the interior of the user's cheeks and behind and internally by the gums and teeth of the user's upper and lower jaws. As shown in FIGS. 4 and 9, preferably the upper rim 304 and the lower rim 306 of the retaining wings 110 each include double curve surfaces. The double curve surfaces comprise a concave surface joined to a pair of convex surfaces. In crosssection, the double curve surfaces are formed by the unison of a pair of convex lines to a concave line. Although portions of each double curve surface are symmetrical about a plane 1002 shown in cross-section in FIGS. 10 and 12 passing through or near a center of the retaining wings 110, in presently preferred alternative embodiments other shapes, symmetries, or lack of symmetry can be used. As shown in FIG. 4, preferably the upper, lower, and side rims 304, 306, and 308 that comprise a circular rim 302 allow the retaining wings 110 to substantially conform to the user's transition between the mucous membrane and the gums.

Referring to FIGS. 1–5 and 7, the retaining wings 110 are coupled to the neck 112 at a position intermediate of the anterior section 104 and a proximal rim 130. Alternatively, the retaining wings 110 can be a unitary part of or coupled to the anterior section 104. The retaining wings 110 comprise a pair of substantially flat surfaces 132 that are interconnected at the circular rim 302. Preferably, the retaining wings 110 are comprised of a substantially elastic material. In the presently preferred embodiments, the retaining wings 110 bias the user's lips and the continuous mucous membrane that lines the inner surfaces of the user's cheeks away from the gums and teeth of the user's upper and lower jaws. Preferably, the natural bias of the retaining wings 110 increases as a continuous flow of fluids, such as compressed air through the orifice 108 into the user's mouth. In this presently preferred embodiment, the retaining wings 110 functions like a valve that allows the flow of fluids only through the orifice 108 when the user's labial and buccal vestibule is pressurized. It is this bias that spreads out the cheeks of the user and facilitates the user's orapharynx to relax and open, which facilitates unrestricted fluid flow.

Preferably, the outer periphery of the neck 108 is surrounded by a plurality of rings. Preferably, one of the rings extends away from the orifice and forms the proximal rim 130 that is positioned near the proximal end of the neck 112. Preferably, the rings allow the presently preferred embodiments to couple other devices including, for example, a fluid line such as a compressed gas line.

Figure 6:
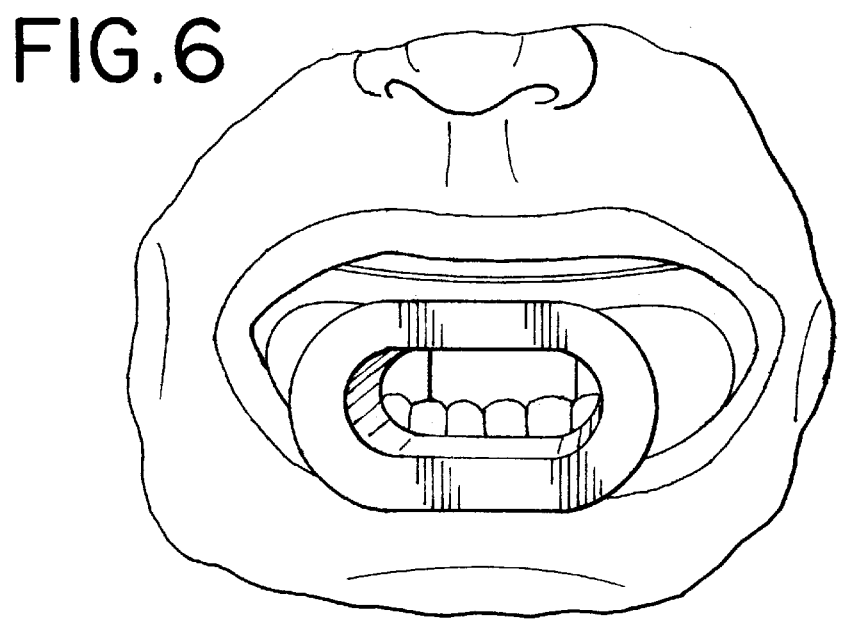
FIG. 6 is a side view of FIG. 1 retained in a user's mouth.
Figure 7:
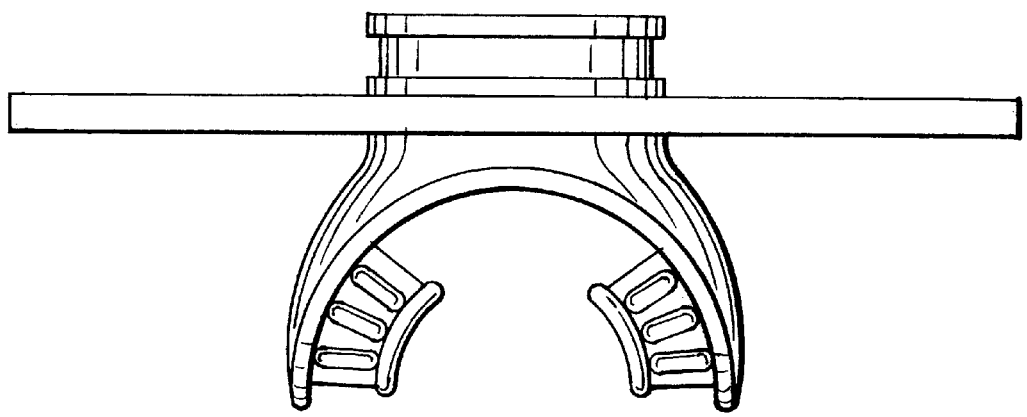
FIG. 7 is a third side perspective view of the presently preferred embodiment of FIG. 1.
Figure 8:
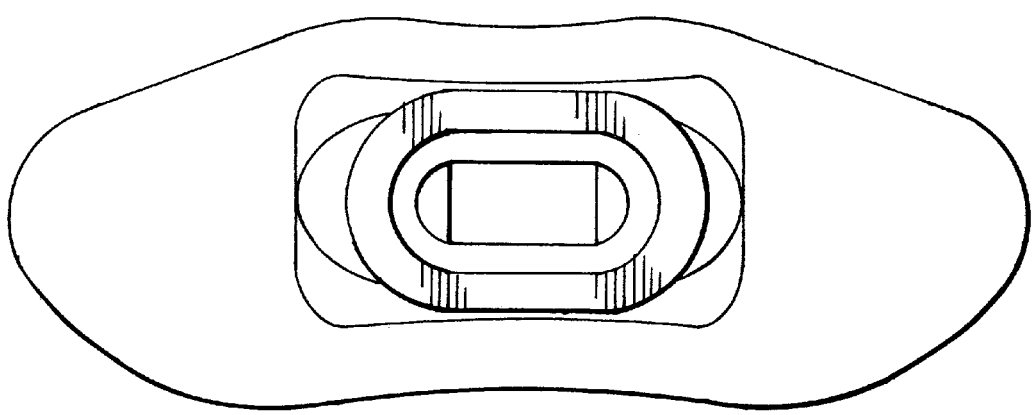
FIG. 8 is a front side view of FIG. 1.

The function of the presently preferred embodiments is illustrated in FIGS. 2, 3, and 6. FIGS. 2 and 3 illustrate the bending of the retaining wings 110 toward the ends 118 of the posterior sections 106. While the retaining wings 110 can be flexed and extended to any length to facilitate a seal or insertion into a user's mouth, as shown the retaining wings 110 extend beyond the ends 118 of the posterior sections 106. Referring to FIGS. 4 and 6, an upper and a lower rim 304 and 306 of the retaining wings 110 are tucked in back of the user's upper and lower lips. Preferably, the side rims 308 of the retaining wings 110 can extend back and adjacent to second or third molars of the user's upper and lower jaws. Preferably when seated in the user's mouth, the bitewings 120 are substantially fitted to the user's occlusal surfaces of one or more bicuspids and/or molars.

Although the claims are not limited to specific dimensions, FIGS. 10–12 illustrate the dimensions of a presently preferred exemplary embodiment. Preferably, L1 is the distance between a side surface of the neck 112 and the side rim 308. Preferably, L2 is the longest distance between an upper surface of the neck 112 and the upper rim 304 and L3 is the longest distance between a lower surface of the neck 112 and the lower rim 306. Preferably, L4 is the distance that separates the ends 118 of the posterior sections 106. Preferably, L5 is the distance between the ends 118 of the posterior sections 106 and a first side surface of the retaining wing 110. Preferably, L6 is the distance between an end of the proximal rim and a second side surface of the retaining wing 110. Preferably, L7 is the distance of a recess positioned between the proximal rim 130 and a second rim. Preferably, L8 is the width of the retaining wing 110. Preferably, L9 is the longest distance between the upper and lower rims 304 and 306. Preferably, L10 is the distance between side rims 308. In the exemplary embodiment illustrated in FIGS. 10–12, L1 is about 48 mm, L2 and L3 are about 14 mm, L4 is about 48 mm, L5 is about 33 mm, L6 is about 10 mm, L7 is about 4 mm, L8 is about 1.5 mm, L9 is about 46 mm, and L10 is about 130 mm. Many other dimensions are possible as the mouthpiece 100 can be made to many other dimensions.

Figure 5:
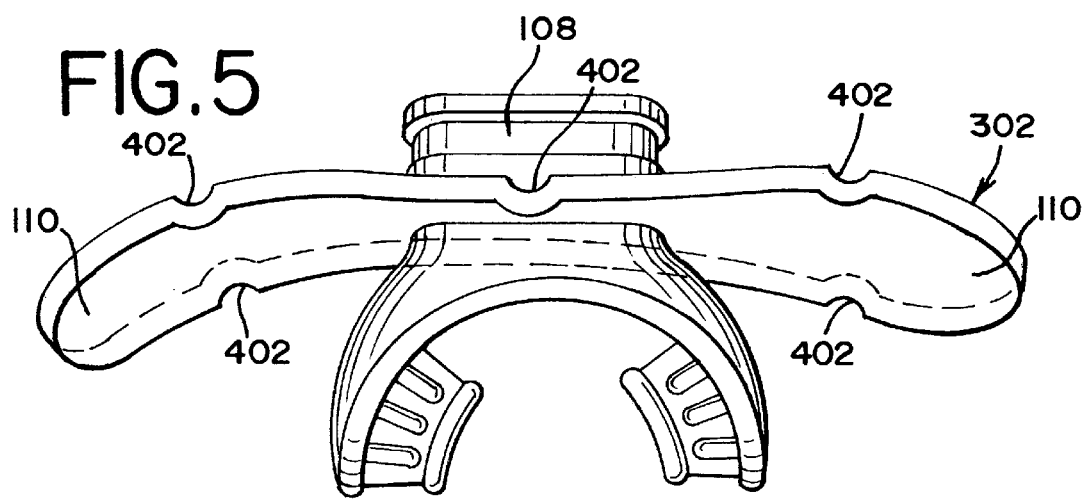
FIG. 5 is a side perspective view of a presently preferred alternative embodiment.

The above-described presently preferred embodiments can be modified into many alternative preferred embodiments. For instance, the retaining wings 110 can be formed of multiple parts and each of the presently preferred retaining wings 110 can assume many other shapes. Preferably, the shape of the retaining wings 110 conforms to the surfaces that bound the labial and buccal vestibule that extends between the user's upper and lower jaws and the interior surfaces of the user's cheeks and lips. Furthermore, as shown in FIG. 5 the circular rim 302 that frames the retaining wings 110 can comprise substantially U-shaped notches 402 at the front and intermediate sections of the retaining wings 110. Preferably, the substantially U-shaped notches 402 can be positioned near the frenum, which are folds of mucous membrane positioned in the front and sides of the user's upper and lower jaws. In yet another presently preferred alternative embodiment, the above-described mouthpiece does not include bitewings 120. In this case, the alternative presently preferred embodiment is retained by the natural bias of the retaining wings 110 and the anterior and posterior sections 104 and 106. Alternatively, when bitewings 120 are used, the upper and lower surfaces 122 and 124 of the bitewings 120 can comprise a self-setting acrylic that conforms to the occlusal surfaces and/or portions of the user's teeth. Similarly, the presently preferred mouthpiece 100 can be customized to a user's mouth or made to selected dimensions.

Moreover, the invention is not limited to the particular retaining wings 110 described above. Any suitable retaining wing can be used. For instance, the circular rim 302 that preferably frames the retaining wings 10 can comprise multiple rims positioned adjacent or spaced apart from one another. Preferably, at least one of the rims forms a seal with the mucous membrane that lines the interior of the user's cheeks and the user's gums. Because a preferred function of one of the rims can be to provide means that facilitates insertion and removal of the presently preferred mouthpiece 100 from a user's mouth, each of the rims can have many other shapes including but limited to elliptical, cylindrical, arcuate, and other curved shapes. In some alternative presently preferred embodiments, at least one of the multiple rims can include U-shaped notches at the front and intermediate sections of the retaining wings 110.

The above-described presently preferred embodiments can be used within many devices including medical, fire fighting, emergency services, and underwater breathing systems. The above-described mouthpieces can be a unitary part or integrated within a standard, modular, or self-contained anesthetic system, firefighter breathing system, ventilator, snorkel, regulator, and scuba system or other underwater, emergency, and medical breathing systems. The above-described presently preferred embodiments can be used with an open or closed breathing system and can be retained in a passive manner that does not require a biting force for mouthpiece 100 retention. Preferably, the presently preferred embodiments are retained in a user's mouth even when a user's jaw muscles are relaxed. Thus, the presently preferred embodiments facilitate a continuous fluid flow even when not retained by a biting pressure. When receiving a pressurized fluid flow through the orifice 108, the presently preferred embodiments maintain a positive pressure seal between the users lips and the continuous mucous membrane that lines the interior of the user's cheeks and the retaining wings 110. Preferably, the presently preferred embodiments provide a watertight seal between the user's labial and buccal vestibule and the user's oral cavity when the preferred mouthpiece 100 is used underwater and a variable or airtight seal when the preferred mouthpiece 100 is used in firefighting, emergency, and/or medical applications.

While various embodiments of the invention have been described, it will be apparent to those of ordinary skill in the art that many more embodiments and implementations are possible that are within the scope of this invention. Accordingly, the invention is not to be restricted except in light of the attached claims and their equivalents.

I claim:

1. A mouthpiece comprising:
   a continuous wall having an anterior and a plurality of posterior sections, the anterior and posterior sections having an inner surface that conforms to an anatomy of a user's upper and lower dental arches, the anterior section enclosing an orifice; and
   retaining wings coupled to the anterior section, a first portion of the retaining wings enclosing a portion of the orifice, and a second portion of the retaining wings substantially conforming to the anatomy of the user's labial and buccal vestibule.

2. The mouthpiece of claim 1 wherein the retaining wings comprise a unitary part of the anterior section.

3. The mouthpiece of claim 1 further comprising a rim surrounding a periphery of the orifice.

4. A mouthpiece comprising:
   a continuous wall having an anterior and a plurality of posterior sections, the anterior and posterior sections having an inner surface that conforms to an anatomy of a user's upper and lower dental arches, the anterior section enclosing an orifice
   a rim surrounding a periphery of the orifice; and
   retaining wings coupled to the anterior section, the retaining wings having a generally flat portion that substantially conforms to the anatomy of the user's labial and buccal vestibule, wherein the retaining wings are coupled to a neck at a position intermediate of the rim and the anterior section.

5. The mouthpiece of claim 1 wherein the retaining wings comprise a substantially circular rim that conforms to the anatomy of a transition between the user's cheeks and gums.

6. The mouthpiece of claim 5 wherein the circular rim comprises U-shaped notches positioned near front and intermediate sections of the retaining wings.

7. The mouthpiece of claim 1 wherein the retaining wings comprise a substantially obround shape.

8. The mouthpiece of claim 1 wherein the retaining wings are configured to provide a watertight seal with the user's labial and buccal vestibule.

9. A mouthpiece comprising:
   a continuous wall having an anterior and a plurality of posterior sections, the anterior and posterior sections having an inner surface that conforms to an anatomy of a user's upper and lower dental arches;
   a neck projecting from the anterior section enclosing an orifice;
   a rim enclosing a proximal end of the orifice;
   a bitewing coupled to each inner surface of the posterior sections; and
   retaining wings coupled to the neck at a position intermediate of the rim and the anterior section, the retaining wings having a generally obround shape that substantially conforms to the anatomy of the user's labial and buccal vestibule.

10. The mouthpiece of claim 9 wherein the retaining wings are configured to provide a watertight seal with the user's labial and buccal vestibule.

11. A mouthpiece comprising:
    a first continuous wall having an anterior and a plurality of posterior sections, the anterior and posterior sections having an inner surface that conforms to an anatomy of a user's upper and lower dental arches;
    a neck enclosing a portion of an orifice and projecting from the anterior section;
    a proximal rim enclosing a portion of the orifice;
    a bitewing coupled to each inner surface of the posterior sections, the bitewings projecting from the inner surfaces of the posterior sections;
    a second wall coupled to each bitewing, the second wall being spaced apart from the inner surface of at least one of the posterior sections; and
    retaining wings coupled to the neck between the proximal rim and the anterior section, the retaining wings that substantially conforms to the anatomy of the user's labial and buccal vestibule.

12. The mouthpiece of claim 11 wherein the bitewings comprise a substantially flat surface coupled to a curved transition.

13. The mouthpiece of claim 12 wherein the second wall is coupled to the curved transition and the second wall substantially conforms to the anatomy of the user's interior dental arch.

14. The mouthpiece of claim 12 wherein the second wall abuts at least one of the user's molars and bicuspids.

15. The mouthpiece of claim 11 wherein the mouthpiece is a scuba mouthpiece.

16. A mouthpiece comprising:
a first continuous wall having an anterior and a plurality of posterior sections, the anterior and posterior sections having an inner surface which conforms to an anatomy of a user's upper and lower dental arches, the anterior section enclosing an orifice;
a neck projecting from the anterior section;
a proximal rim enclosing a proximal end of the orifice;
a bitewing coupled to each inner surface of the posterior sections, the bitewings projecting from the inner surfaces of the posterior sections and substantially conforming to the anatomy of selected occlusal surfaces of the user's teeth;
a second wall coupled to each bitewing, the second wall being spaced apart from the inner surface of at least one posterior section, the second wall being coupled to at least one curved transition and conforming generally to the anatomy of at least one of the user's interior upper and lower dental arches; and
retaining wings coupled to the anterior section, the retaining wigs substantially conforming to the anatomy of the user's labial and buccal vestibule, and wherein a portion of the retaining wings enclose a portion of the orifice.

17. The mouthpiece of claim 16 wherein the retaining wings comprise a top and a bottom rim each comprising a concave and a plurality of convex surfaces.

18. The mouthpiece of claim 16 wherein the continuous wall, bitewings, and retaining wings are a unitary part of the mouthpiece.

19. The mouthpiece of claim 16 wherein the mouthpiece comprises a scuba mouthpiece.

20. A scuba mouthpiece comprising:
a first continuous wall having an anterior and a plurality of posterior sections, the anterior and posterior sections having an inner surface that conforms to an anatomy of a user's upper and lower dental arches, the anterior section enclosing an orifice;
a neck projecting from the anterior section;
a bitewing coupled to each inner surface of the posterior sections; and
retaining wings coupled to the anterior section, the retaining wings substantially conforming to the anatomy of the user's labial and buccal vestibule, wherein the retaining wings comprise a top and a bottom rim that each have concave and convex surfaces and wherein a portion of the retaining wings enclose the neck.

21. A mouthpiece comprising:
a first continuous wall having an anterior and a plurality of posterior sections;
a neck enclosing an orifice projecting from the anterior section; and
retaining wings coupled to the nor section, the retaining wings having a first portion that encloses a portion of the orifice and a second portion that substantially conforms to an anatomy of a user's labial and buccal vestibule that extends between the user's upper and lower jaws and interior surfaces of the user's cheeks.

22. A method of using a mouthpiece comprising
grasping a continuous wall having an anterior and a plurality of posterior sections, the anterior and posterior sections having an inner surface which conforms to an anatomy of a user's upper and lower dental arches, the anterior section enclosing an orifice;
flexing a pair of retaining wings toward ends of the posterior sections, the retaining wings having a generally obround shape that conforms to the anatomy of the user's labial and buccal vestibule, a portion of the retaining wings enclosing a portion of the orifice; and
inserting the retaining wings into the user's mouth.

23. The method of inserting a mouthpiece of claim 22 further comprising connecting a fluid line to an orifice passing through the continuous wall.

24. The method of inserting a mouthpiece of claim 23 further comprising actuating the flow of a fluid through the orifice.

25. A method of using a mouthpiece comprising
grasping a first continuous wall having an anterior and a plurality of posterior sections, the anterior and posterior sections having an inner surface which conforms to an anatomy of a user's upper and lower dental arches, the anterior section enclosing an orifice;
flexing a pair of retaining wings toward ends of the posterior sections, the retaining wings having a first portion that encloses the orifice and a second portion that conforms to the anatomy of the user's labial and buccal vestibule; and
inserting bitewings and the retaining wings into the user's mouth; and
retaining the mouthpiece in the user's mouth while the mouthpiece is at least partially submerged in water.

26. A method of using a mouthpiece comprising
grasping a first continuous wall having an anterior and a plurality of posterior sections, the anterior and posterior sections having an inner surface which conforms to an anatomy of a user's upper and lower dental arches, the anterior section enclosing an orifice;
flexing a pair of retaining wings toward ends of the posterior sections, the retaining wings having a first portion that encloses the orifice and a second portion that conforms to the anatomy of the user's labial and buccal vestibule;
inserting bitewings and the retaining wings into the user's mouth; and
retaining the mouthpiece in the user's mouth while the user receives a medical treatment.

27. A mouthpiece comprising:
a continuous wall having an anterior and a plurality of posterior sections, the anterior and posterior sections having an inner surface that conforms to an anatomy of a user's upper and lower dental arches, the anterior section enclosing an orifice; and
retaining wings being directly adjacent to and coupled to the anterior section, a portion of the retaining wings having a portion substantially conforming to the anatomy of the user's labial and buccal vestibule.

28. The mouthpiece according to claim 27 wherein the retaining wings comprise a one-piece structure.

* * * * *

UNITED STATES PATENT AND TRADEMARK OFFICE
CERTIFICATE OF CORRECTION

PATENT NO. : 6,536,424 B2
DATED : March 25, 2003
INVENTOR(S) : Russell P. Fitton It is certified that error appears in the above-identified patent and that said Letters Patent is hereby corrected as shown below:

Column 7,
Line 55, before "section," delete "nor" and substitute -- anterior -- in its place.

Signed and Sealed this

Twenty-third Day of March, 2004

JON W. DUDAS
*Acting Director of the United States Patent and Trademark Office*